(12) United States Patent
Franklin et al.

(10) Patent No.: US 7,389,186 B2
(45) Date of Patent: Jun. 17, 2008

(54) PREDICTION OF STREAM COMPOSITION AND PROPERTIES IN NEAR REAL TIME

(75) Inventors: Howard D. Franklin, Silver Spring, MD (US); Apostolos T. Georgiou, Reston, VA (US); J. Douglas Kushnerick, Warren, NJ (US); Helen S. Wellons, Mount Laurel, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 11/502,428

(22) Filed: Aug. 11, 2006

(65) Prior Publication Data

US 2008/0040051 A1  Feb. 14, 2008

(51) Int. Cl.
*G01N 31/00* (2006.01)
(52) U.S. Cl. .......................................... 702/27
(58) Field of Classification Search ................. 702/27; 324/303; 356/70
See application file for complete search history.

(56) References Cited

U.S. PATENT DOCUMENTS

| | | | |
|---|---|---|---|
| 5,402,333 A | 3/1995 | Cardner | |
| 5,504,692 A | 4/1996 | Cardner | |
| 6,087,662 A | 7/2000 | Wilt et al. | |
| 6,317,654 B1 | 11/2001 | Gleeson et al. | |
| 6,442,513 B1 | 8/2002 | Cheng et al. | |
| 6,490,029 B1 * | 12/2002 | Cho et al. | ...................... 356/70 |
| 6,611,735 B1 | 8/2003 | Henly et al. | |
| 2003/0004696 A1 | 1/2003 | Yamazaki et al. | |
| 2003/0097194 A1 | 5/2003 | Gade et al. | |
| 2003/0097243 A1 | 5/2003 | Mays et al. | |
| 2004/0019437 A1 | 1/2004 | Keleman et al. | |
| 2004/0220716 A1 * | 11/2004 | Yokohata et al. | ............ 701/102 |
| 2005/0242807 A1 * | 11/2005 | Freedman | .................... 324/303 |
| 2006/0218311 A1 * | 9/2006 | Maranat et al. | ................ 710/19 |

FOREIGN PATENT DOCUMENTS

WO  WO 0125863  4/2001

* cited by examiner

*Primary Examiner*—John E Barlow, Jr.
*Assistant Examiner*—Xiuquin Sun
(74) *Attorney, Agent, or Firm*—W. Robinson H. Clark

(57) ABSTRACT

The invention provides a method and means of predicting, in near real-time, the detailed chemical composition of major streams in a refinery, including those downstream from the crude distillation column. The dynamically updated feed characterizations can be derived in near real time from an assay database of current crude diet, RTO information about upstream refinery units and various analyzer inputs. The chemical compositions of each stream are stored and updated in a plant wide database. A broad range of property calculations can be ascertained, either automatically or on demand, from the compositional information. An application permits users, such as operations, planning and engineering personnel, to access the database directly or indirectly (e.g., on line). This information is then used by each user to further optimize the operation of a given refinery unit and/or the plant as a whole.

19 Claims, 4 Drawing Sheets

ARCHITECTURE OF ROC SYSTEM

Typical Atmospheric Crude Distillation Column

Typical Atmospheric Crude Distillation Column ROC Engine

US 7,389,186 B2

PREDICTION OF STREAM COMPOSITION AND PROPERTIES IN NEAR REAL TIME

1.0 BACKGROUND OF THE INVENTION

1.1 Field

The field of the invention is apparatuses and methods for predicting the composition and properties of streams in a petroleum refinery. More particularly, the invention is directed to apparatuses and methods for generating on-line, near real-time, dynamically updated predictions of the composition and properties of a given stream.

1.2 Description of Related Art

Crude oil, or petroleum, is a complex multi-component mixture of various hydrocarbons and compounds containing nitrogen, oxygen and sulfur. Most crude oil also contains minor amounts of nickel and vanadium.

The exact chemical composition of a given crude oil will vary significantly depending on its point of origin. As a result, the chemical and physical properties of crude oil vary. Crude oil itself is rarely used as a fuel because (a) its properties are too variable and (b) its properties do not meet the specifications of most furnaces, boilers and engines. Processing crude oil into more useful fuels and other petroleum based products is relatively complex and refinery operations vary greatly. However, at a high level, a number of commonalities exist. First, in a typical refinery, crude oil purchased on the open market is stored and commingled in storage tanks until processing. Thus, the initial crude oil feed is often a mixture of different crude oils. Second, the feed is heated on its way to an atmospheric distillation unit (a.k.a. atmospheric pipestill or "APS"). A typical APS tower, or column, comprises a series of trays, liquid side draws, pump arounds, and a condenser. The APS tower distills the feed at atmospheric pressure and separates the feed into fractions, or cuts, each cut being equivalent in boiling range to one desired product, e.g., gasoline, naphtha, kerosene, light gas oil (LGO), heavy gas oil (HGO) and residue. Third, each fraction, or cut, is removed as a stream through a liquid side draw in the APS tower. The streams removed from the APS tower through the liquid side draws can be sold as finished products or blended with other streams and/or further processed to increase economic value. For example, high boiling APS products such as kerosene, LGO, HGO and residue can be converted into lower boiling products such as gasoline by subjecting the streams to further distillation in a vacuum pipestill (VPS) followed by thermal cracking and/or catalytic cracking in a fluid catalytic cracking (FCC) unit.

Alternatively or in addition, catalytic reforming, isomerization, alkylation, polymerization, hydrogenation, and various other operations and combinations thereof can be used to upgrade streams into higher value products.

Based on supply and demand, the value of any given petroleum product will change on a daily basis. Furthermore, different crude oils and intermediate streams, because of their composition, are better suited to make different products. Finally, the pressures, temperatures and flow rates that are ideally suited to successfully process each stream in a refinery process vary depending on the composition of the stream. Refineries are constantly seeking better ways to optimize the operation of each unit in the process to better achieve the optimal balance between the amount and value of petroleum products produced and the production expenses incurred.

In the petrochemical industry, extremely detailed analyses of feed and product materials (assays) are often utilized for making business decisions, for planning, controlling and optimizing operations and for certifying products. Chief among these analyses is the crude assay. When a crude oil is assayed, it is distilled in two steps. A method such as ASTM D2892 (see Annual Book of ASTM Standards, Volumes 5.01-5.03, American Society for Testing and Materials, Philadelphia, Pa.) can be used to isolate distillate cuts boiling below approximately 650° F. (343° C.). The residue from this distillation is further distilled using a method such as ASTM D5236 to produce distillate cuts covering the range from 650° F. to approximately 1000-1054° F. (343° C. to 538-568° C.) and a vacuum residue cut. At a minimum, cuts corresponding to typical products or unit feeds are typically isolated that include following: liquefied petroleum gases (LPG) at initial boiling point to 68° F. (20° C.); light straight run naphtha (LSR) at 68° F. to 155° F. (20° C. to 68.3° C.); heavy straight run naphtha (HSR) at 155° F. to 350° F. (68.3° C. to 176.7° C.), kerosene at 350° F. to 500° F. (176.7° C. to 260° C.), diesel at 500° F. to 650° F. (260° C. to 343.3° C.), vacuum gas oil at 650° F. to 1000° F. (343.3° C. to 537.8° C.); and vacuum residue at 1000° F. to 1054° F. (537.8° C. to 567.8° C.). Each distillate cut is then analyzed for elemental, molecular, physical and/or performance properties. The specific analyses conducted depend on the typical disposition of the cut. Example analyses are known in the art and extensively discussed and tabulated in, inter alia, U.S. Pat. No. 6,662,166.

Depending on the intended use of the crude assay data, different organizations will employ different assay strategies. For compositional and process modeling, extremely detailed analyses, mapping thousands of molecules, may be employed. For example, the high detail hydrocarbon analysis (HDHA) method described by Jacob, Quann, Sanchez and Wells (Oil and Gas Journal, Jul. 6, 1998) can be employed.

A detailed crude assay using a process, such as HDHA, costs many thousands of dollars and takes weeks to complete. As a result, the assay data used for making business decisions, and for planning, controlling and optimizing operations, is seldom from the cargoes currently being bought, sold or processed but rather historical data for "representative" past cargoes.

More recently, Exxon Mobil Corporation's virtual assay technology has dramatically lowered the time and expense to obtain a detailed crude assay to a few hours and a few hundred dollars. Virtual assay compares spectral data to a library of historical spectra and other information and is described, inter alia, in U.S. Pat. No. 6,662,116 issued Dec. 9, 2003, the entire contents of which are hereby incorporated by reference.

The crude assay data will typically be stored in an electronic database where it can be mathematically manipulated to estimate crude qualities for any desired distillation range. For example, commercial crude assay libraries are available from Haverly Systems Inc. and HPI Consultants Inc.—both of which provide tools for manipulating the data, as does Aspentech Inc. Assay data is published by Crude Quality Inc., by Shell Oil Company and by Statoil. The property versus distillation temperature data is typically fit to smooth curves that can then be used to estimate the property for any desired distillation cut.

The on-line optimum operation of the crude distillation column, blending units, and downstream process units can result in significant economic benefits. A real time optimization (RTO) system, which runs on an on-line process control computer and automatically calculates and implements the optimization results, can be used to keep each phase of the plant operation close to the economic optimum. The cornerstone of any successful RTO system is feed characterization information and the process models upon which the calculations are based. Accuracy of the process models must be sufficient to predict the actual process interactions and constraints.

Unfortunately, effective on-line RTO of crude distillation columns requires the lumping of detailed assay feed characterizations into boiling point cuts. In other words, there are about 10,000 or so different molecular species in crude oil. The model used in the RTO of the crude distillation column is unable to include all of these species. As a result, a major simplification is made. The species are grouped together into "cuts." Each cut has a specific boiling point range. Thus, for example, all of the molecular species whose boiling point lies between 330° F. (165.6° C.) and 350° F. (176.7° C.) might be combined together into a single component known as a 340° F. (171.1° C.). This greatly reduces the number of species needed in the crude distillation column RTO. It also gives a component breakdown that is "good enough" for the crude distillation column RTO as the crude distillation column is mostly concerned with the boiling points of the components that it processes.

Therefore, detailed assay feed characterizations are unavailable to downstream RTO applications—which rely instead on static feed reference characterizations that are then tuned to current bulk properties and product yields. In other words, a static representative feed is characterized for a given downstream unit and then used as the reference for all feeds to the unit. The downstream RTO systems then tunes the static feed as needed to match current measured bulk properties, yields, or operating conditions. This static feed reference characterization, because it is not based on updated feed characterization information, often leads to sub-optimal solutions and non-robust behavior. This is becoming a problem as refineries struggle to meet stricter environmental laws and regulations governing fuel components such as sulfur.

It would be desirable to develop more dynamically updated feed characterizations for downstream process and blending RTO systems. This would permit enhanced optimization of refining processes.

2.0 BRIEF DESCRIPTION OF THE SEVERAL VIEWS OF THE DRAWINGS

The drawings are for illustration purposes only and are not intended to limit the scope of the invention.

FIG. 1 illustrates the method steps for one embodiment of the invention.

FIG. 2 provides an illustrative architecture for applications used in one embodiment of the invention.

3.0 SUMMARY OF THE INVENTION

Figure 1:
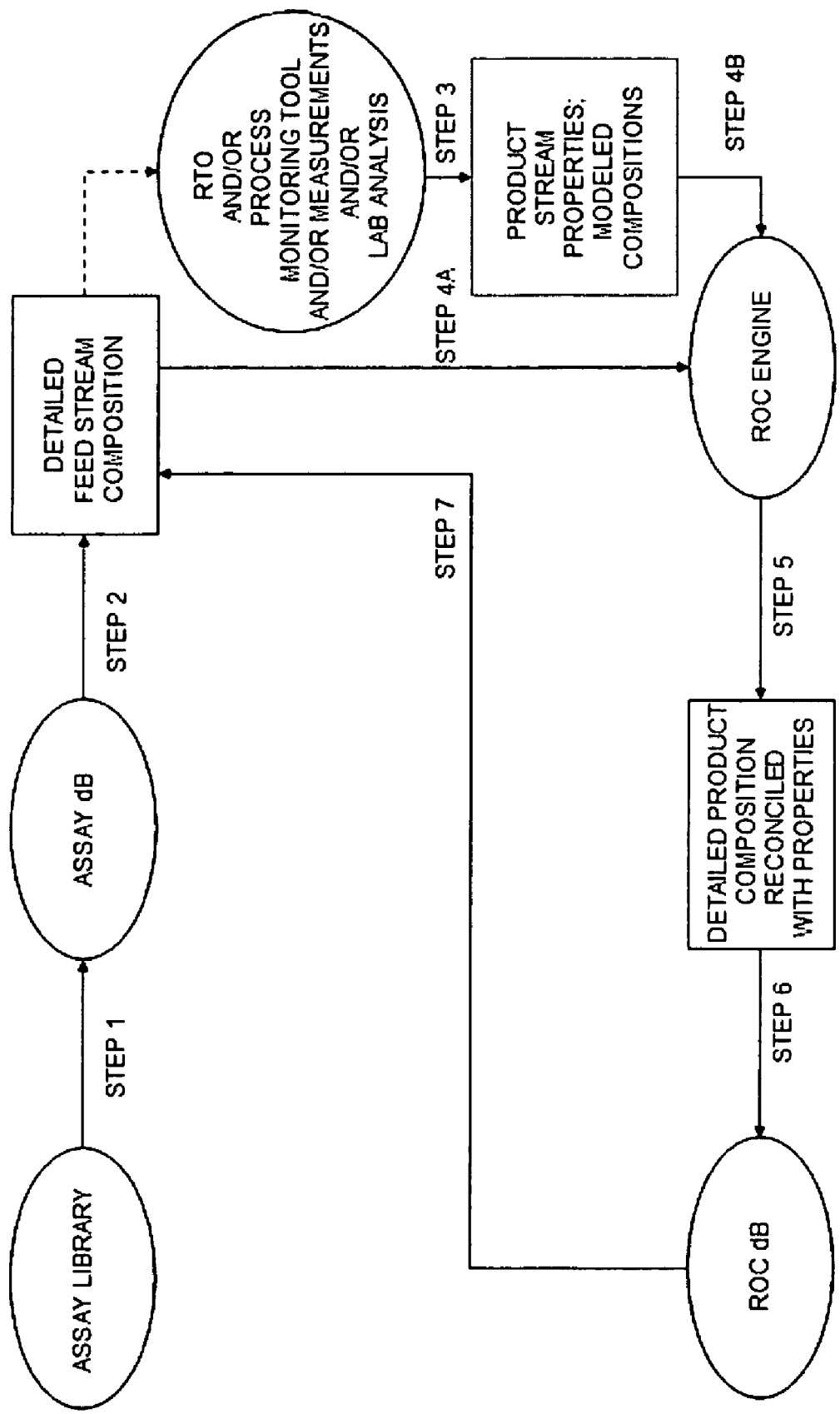

The invention provides a method and means of predicting, in near real-time, the detailed chemical composition of major streams in a refinery, including those downstream from the crude distillation column. The dynamically updated feed characterizations can be derived in near real time from an assay database of current crude diet, RTO information about upstream refinery units and various analyzer inputs. The chemical compositions of each stream are stored and updated in a plant wide database. A broad range of property calculations can be ascertained, either automatically or on demand, from the compositional information. An application permits users, such as operations, planning and engineering personnel, to access the database directly or indirectly (e.g., on line). This information is then used by each user to further optimize the operation of a given refinery unit and/or the plant as a whole. Many refinery functions benefit from access to accurate detailed information about stream compositions. Such information can be used, inter alia, for following purposes: (a) to make better decisions when optimizing particular chemical properties in a stream, e.g., sulfur content; (b) to better monitor the health and reliability of equipment by providing a more accurate understanding of the equipment's operating environment; and (c) to enhance the accuracy of compositional based RTOs throughout the plant with more accurate inputs.

4.0 DETAILED DESCRIPTION OF THE INVENTION

4.1 Definitions

The following words and phrases have the following meanings:

"Application" or "application program" means a computer program, or a collection of computer programs, that performs a function not related to the computer itself.

"Lumping" is a process by which data on the molecular population of a stream is substantially reduced ("lumped"), generally by an application using an algorithm, to a more manageable form by grouping the data into groups called lumps. For example, structure oriented lumping (SOL) is a known means in the art for lumping stream components. (See, e.g., Quann, R. J., Jaffe S. B., Structure-oriented lumping: describing the chemistry of complex hydrocarbon mixtures, I&EC Res 31:2483-2497 (1992), the entirety of which is incorporated herein by reference.) Conversely, "delumping" is a process where lumped data is expanded again ("delumped"), usually by reversing the operations performed by the original lumping algorithm.

"Process unit" means any device in a crude oil refinery that treats a feed stream to generate one or more product streams having a different chemical composition from the feed stream. In example, process units include atmospheric distillation units, vacuum distillation units, naphtha hydrotreater units, catalytic reformer units, distillate hydrotreater units, fluid catalytic cracking units, hydrocracker units, alkylation units and isomerization units.

"Process monitoring tool" means an application that models a process unit and the product streams produced thereby (generally including thermodynamic and/or kinetic properties) without reconciling predicted results with actual process unit or product stream data.

"Processor" means a processing unit, or a collection of processing units, that run a given application.

"Real time" means on demand.

"Real time optimization application" or "RTO application" means an application that determines, in near real time, optimized set points for a process unit by modeling the process unit and the product streams produced thereby (generally including thermodynamic and/or kinetic properties), reconciling predicted results with actual process unit and/or product stream measurements, and optimizing the performance of the process unit to maximize certain results and minimize certain results.

"Shadow model" means a molecular accounting tool that mimics the movement of molecular components in a process without performing kinetic or thermodynamic calculations.

"Stream" means any gas, liquid or semi-liquid in a refinery flowing to or from a process unit. In example, "stream"

includes crude oil as well as LPG, LSR, HSR, kerosene, diesel, vacuum gas oil, vacuum residue and precursors thereof.

"Upstream" means on the stream in the direction opposite the flow of the stream. Conversely, "downstream" means on the stream in the direction of the flow of the stream.

4.2 The Rigorous On-Line Composition (ROC) Method

The invention is a collection of applications that perform a method of predicting, dynamically, in near real-time, the molecular composition of streams in a crude oil refinery. The method, referred to herein as the Rigorous On-Line Composition (ROC) method, is described below with reference to FIG. 1.

Step 1 in FIG. 1 comprises obtaining detailed information regarding the composition of a potential crude oil feed streams to a refinery, as well as physical properties of the streams that cannot be calculated from composition alone (e.g., temperature, pressure, and mass flow) and then storing said information in a crude assay database. This information can be input directly or pulled from any crude assay library (e.g., ExxonMobil's Compass database that contains HDHA data for various crude oils). The composition and property information for each potential crude oil is formatted and stored in the crude assay database in accordance with a pre-defined template. In other words, each crude oil is described in the crude assay database as a subset of the predefined template. For example, if a given crude oil has 10,000 components, but only 8,000 components can be characterized in the template, the 10,000 components in the crude oil will be lumped to form a subset that represents the best fit with the 8,000 components in the template. Similarly, if a crude oil has 7,000 components, any component in the template missing from the stream will be recorded in the subset as being present in zero quantity (i.e., absent) and any component in the stream that does not conform with a component in the template will be recorded as the component in the template that provides the closest fit.

Ideally, the template characterizes a sufficient number of molecular components in sufficient detail to provide or derive any and all data needed by any real time optimization application, off-line process monitoring tool, shadow model and/or bulk property correlation that pulls molecular component data or property data from the crude assay database. Accordingly, the template provides significant sorting information about the various molecular components in each crude oil. For example, in one embodiment, the template describes molecules by the number and type of atoms (e.g., carbon, oxygen, nitrogen, sulfur and various metals) present therein and the number, type and location of certain molecular moieties (e.g., olefin and diolefin moieties, aromatic bonds, and saturated and unsaturated rings) present therein. Preferably, the template is highly detailed, meaning that it characterizes over 1000 molecular components, more preferably over 2500 molecular components and even more preferably over 5000 molecular components.

Each subset associated with each potential crude oil feed is stored in the crude assay database using a unique identifier. Accordingly, a subset description of a crude oil can be pulled from the crude oil database using the unique identifier associated with the subset.

Step 2 in FIG. 1 comprises obtaining detailed data on the molecular components and non-compositional based physical properties of actual feed streams flowing to a predefined window of refining operations comprising a process unit during a given time period. For example, feed streams to an APS unit are primarily virgin crude oil and recycle streams. If a feed stream to an APS unit during the given time period is a virgin crude oil, the detailed data on the feed stream is pulled from the crude assay database described in Step 1 using the unique identifier associated with the crude oil's subset description. Alternatively, if a feed stream to an APS unit during the given time period is a recycle stream, the detailed data on the feed stream is pulled from a product stream database that is populated in subsequent steps of this method, using a unique identifier and timestamp associated with a subset description of the recycle stream. Regardless, the data on the feed stream is obtained in the form stored, i.e., as a subset of the template described in Step 1 above.

Step 3 in FIG. 1 comprises obtaining property data from actual intermediate and/or product streams produced in, or by, the predefined window of refining operations during the given time period. This step can be performed using RTO applications, lab analysis, on-line measurements, or any combination thereof.

In one embodiment of Step 3, an RTO application is employed to obtain intermediate and/or product stream properties and, optionally, product stream composition data. For example, an APS RTO application models an APS unit, reconciles predicted performance of the unit with actual unit information including stream properties and then optimizes the performance of the unit. The output of such an RTO can include, inter alia, reconciled plant measurements, intermediate and final product stream properties, and lumped intermediate stream and final product compositions.

In another embodiment of Step 3, property data on intermediate and/or product streams can be obtained by direct measurement and/or laboratory analyses of intermediate and/or product streams. This alternative is most often employed when an RTO for the process unit is not available.

Step 4A in FIG. 1 comprises communicating, to a processing engine that runs models of the predefined window of refinery operations, detailed data on feed stream composition and non-compositional based feed stream properties. In FIG. 1, as would be the case when the ROC method is employed with an APS unit, this data is the data obtained in Step 2. Alternatively, this data can come from upstream analyzers (e.g., FTIR-virtual assay). Alternatively, when the predefined window of operations being modeled comprises a reactor that performs actual chemical conversion (e.g., the riser in an FCC unit), as opposed to simple separation (e.g., an APS unit), and an RTO or off line process monitoring tool for the reactor generates an accurate and detailed representation of product stream composition, then the data from the RTO or off line process monitoring tool can be delumped, translated to the template, and communicated to a processing engine that models subsequent steps in the window of refinery operations (e.g., distillations).

Step 4B in FIG. 1 comprises communicating, to the same processing engine, the property data obtained in Step 3 on actual intermediate and/or product streams produced in, or by, the predefined window of refining operations.

Step 5 in FIG. 1 comprises running the processing engine to obtain a detailed prediction of product stream composition that is reconciled with actual intermediate and/or product stream property measurements. The processing engine comprises one or more short cut programs, called shadow models. Each shadow model is a molecular accounting tool that accounts for how molecules move through the predefined window of refinery operations including the process unit (e.g., tank models, mixer models, splitter models, component splitter models and cut models) without making complicated thermodynamic or kinetic calculations. By avoiding thermodynamic and kinetic calculations, the amount of composition parameters that can be processed within a suitable computation time (e.g., preferably less than thirty minutes) rises dramatically. Thus the short cut shadow models can process detailed stream characterizations of over 1000, preferably over 2500 and more preferably over 5000 molecular components in a relatively short period of time.

The processing engine that contains the shadow models performs a two-part process wherein: (a) a prediction of product stream composition is obtained by running each shadow model to account for various changes in composition performed by each operation within the predefined window of refinery operations; and (b) the prediction of product stream composition is reconciled with actual intermediate and/or product stream properties. The input to the first shadow model in the processing engine is the detailed data on the feed stream (e.g., obtained in Step 2) above which was communicated to the processing engine in Step 4A above. The input for any subsequent shadow model in the processing engine is the output for the immediately preceding shadow model. The output for the last shadow model in the processing engine is a detailed prediction of product stream composition, expressed as a subset of the template. To reconcile the prediction with actual intermediate and/or product stream properties, the processing engine uses the intermediate and/or product stream properties obtained in Step 3 above which were communicated to the processing engine in Step 4B above. More specifically, predicted intermediate and/or product stream properties are calculated by the processing engine based on the predicted composition and compared to the actual intermediate and/or product stream properties. Fixed model parameters in the shadow models are then adjusted to minimize the difference between the predicted intermediate and/or product stream properties and the actual intermediate and/or product stream properties. Adjusting the fixed model parameters in the shortcut shadow models modifies the predicted compositions to provide a best fit to the actual product stream properties.

The end result of Step 5 is a detailed prediction of product stream composition, expressed as a subset of the template, reconciled with actual intermediate and/or product stream properties. The prediction, which preferably details the presence or absence of 1,000 or more molecular components in the product stream, is far more detailed than the highly lumped product stream composition information that would be provided, for example, by an APS RTO.

Step 6 in FIG. 1 comprises storing the reconciled prediction of product stream composition obtained in Step 5 above, along with product stream properties, into a product stream database using a unique stream identifier and timestamp. The data is then retrievable from the product stream database, using the unique stream identifier and timestamp, for use in modeling and optimizing downstream operations. The product stream database illustrated in FIG. 1 is separate from the crude assay database. However, this distinction between the databases is not necessary and, in an alternative embodiment, the databases are merged.

Step 7 in FIG. 1 comprises extracting, from the product stream database, using a unique stream identifier and time stamp, information regarding the composition and properties of a product stream. This information can then be used to model and/or optimize one or more downstream refining operations. In this regard, it should be recognized that the product stream from an upstream process unit (e.g., an APS unit) can either form, or be used to form, the feed stream for one or more downstream units. Thus, compositional information about a given product stream from an upstream process unit is useful in determining feed stream input for models of downstream process units.

For example, as shown in FIG. 1 by a dotted arrow, when a stream from the product stream database is used directly as a feed stream to a downstream process unit, the stream composition obtained from the database can be used as an input for an RTO application (or off-line processing model) for the downstream process unit. In this example, the stream composition, which is expressed as a subset of the template, is generally translated (e.g., lumped) and converted into the binary format used by the particular RTO application.

Alternatively or in addition, when there is a series of refinery operations that modify the composition of a stream stored in the product stream database as it travels from an upstream process unit to a downstream process unit, a second processing engine can employ shadow models, in the same manner described above, to model each operation leading to the downstream process unit. The input into the first shadow model in the second processing engine is the composition of the product stream obtained from the product database. The output from the last shadow model in the second processing engine is then the feed stream composition to the process unit and can be used to create the input for an RTO application (or off line processing model) that models the downstream process unit.

The output from the RTO application, which is now based on more dynamic feed references, can then be utilized to update the product stream database. Alternatively, the output from the RTO application, as already discussed in the context of a reactor such as the riser in an FCC process unit, can be used as an input to another processing engine that utilizes shadow models to mimic subsequent refining steps (e.g. distillation).

The method described above can be repeated for any number of downstream refinery operations. The nature of the process units, or any given window of refinery operations, used in the method is not particularly limited. Suitable process units include, for example, additional APS units, vacuum distillation units, naphtha hydrotreater units, catalytic reformer units, distillate hydrotreater units, fluid catalytic cracking units, hydrocracker units, alkylation units, and isomerization units. A reconciled prediction of the composition of each product stream is then used to update the product database for use in modeling operations even further downstream.

The ROC method provides better compositional data for models of refinery operations. The ROC method also provides a supporting architecture for real time optimization of multiple units in a refinery using a plant wide RTO that optimizes plant-wide performance based on the molecular composition of feed streams and products streams to and from each process unit.

Each of the ROC method steps described herein can be performed automatically or on demand. In other words, each of the steps can be performed by an application or collection of applications without the need for human intervention or can be performed by an application or a collection of applications, upon command by a human operator, without the need for further human intervention.

The more frequently the ROC method is performed, the closer the information obtained by the method comes to being real time information. The principle limitation on the frequency in which the ROC method can be run is the frequency in which the on-line analyzers and/or RTOs utilized in the ROC method are run. For example, if the ROC method uses an RTO that runs once an hour, then the ROC method can also be run once an hour. If, however, the RTO is run once every two hours or once every half hour, then frequency the ROC method can be run is doubled or halved, respectively. The ROC method is preferably run at least once every four hours, preferably at least once every two hours, more preferably at least once every hour, and ideally at least once every half hour. The time it takes to run the ROC method itself, once the necessary inputs are available, is dependent on the complexity of the shortcut shadow model reconciliation case, which could include one process unit, or span the entire refinery. In the most complex case, it should run in under one hour, preferably less than thirty minutes and, ideally, in ten to twenty minutes.

4.3 The Rigorous On-Line Composition (ROC) System

The collection of applications that performs the method of predicting, in near real-time, the detailed chemical composition of major streams in a refinery, including those downstream from the crude distillation column, is referred to herein as the Rigorous On-Line Composition (ROC) system. This system is described herein with reference, as appropriate, to FIG. 2, which provides an illustrative architecture for the applications disclosed herein.

Figure 2:
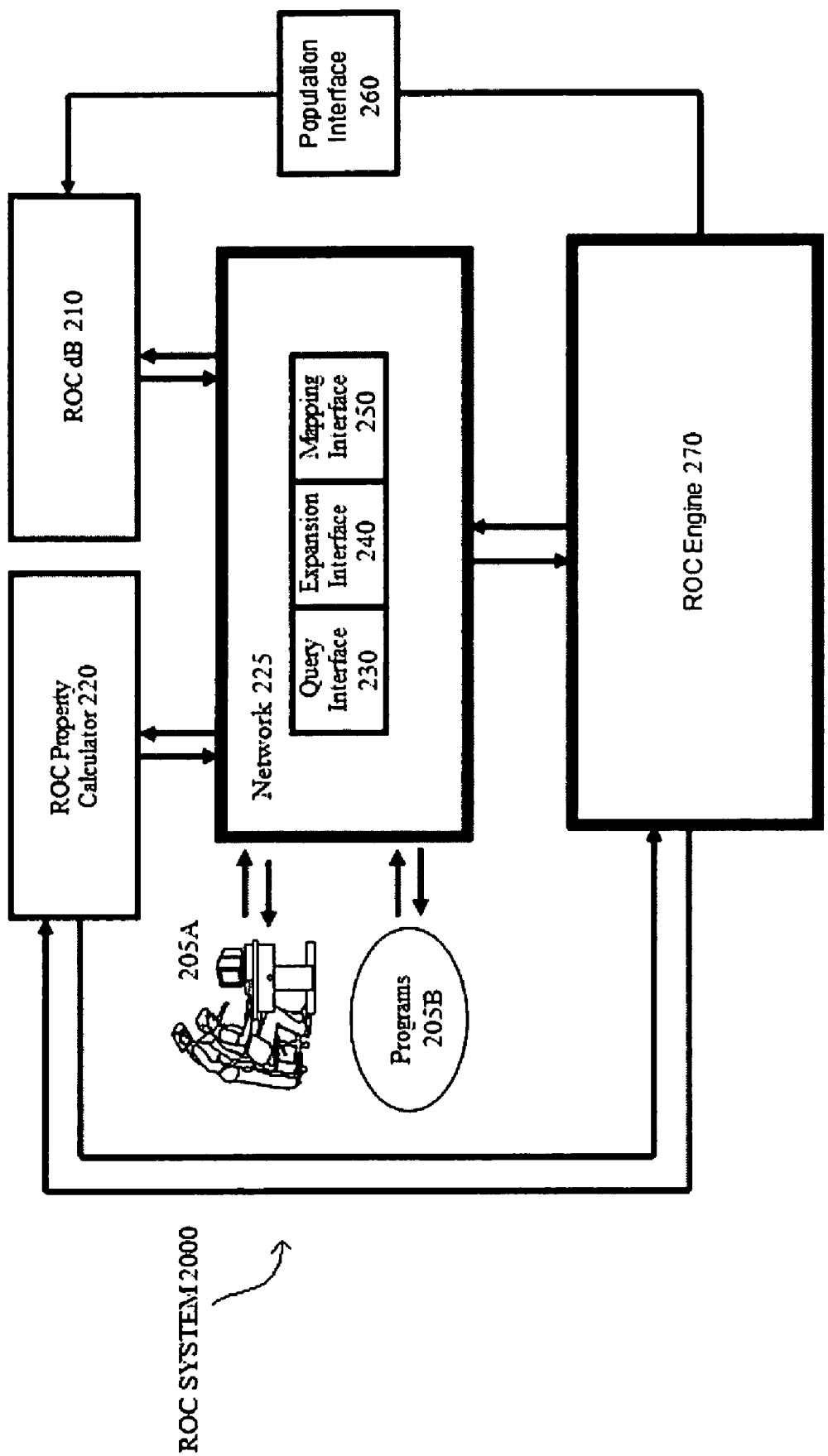

As set forth in FIG. 2, the first component of a ROC system 2000 is a database, referred to herein as the ROC dB 210, that stores information for each of the major refinery streams—although information for virgin crude oil feed streams can, but does not have to be, stored in a separate database. The ROC dB 210 is a read/write database that includes a detailed composition for each stream as well as temperature, pressure, mass flow and various bulk stream properties that cannot be accurately calculated from composition alone. Preferably, this information is stored on a dynamically updated basis. The stream data is retrievable from the database with a unique stream identifier and timestamp associated with each stream.

The detailed composition data stored in the ROC dB 210 for each stream is stored in accordance with a predetermined template (referred to herein as the ROC superset template) which can be as large as desired but must be sufficiently detailed to contain every component required by any application that pulls information from the ROC dB 210. The molecular data is stored in such a way that each entry provides significant sorting information about the molecule represented, e.g., the number and type of atoms (such as the number of carbon, oxygen, nitrogen, sulfur and metal atoms) and the number, type and location of molecular moieties (such as the number and location of olefin moieties, diolefin moieties, aromatic bonds, saturated rings and unsaturated rings). Preferably, the ROC Superset template characterizes over 1000 components, more preferably over 2500 components and even more preferably over 5000 components.

The information stored about each stream is stored as a subset of the ROC superset template (called herein a ROC superset representation). For instance, the ROC superset template may describe an entire assay using 10,000 components. In this case, if the stream is, for example, a naphtha cut, the stream may only have 200 of the components. Therefore, the ROC superset representation of the stream will list a positive value for the 200 components in the ROC superset template present in the stream and a zero value for the 9,800 components in the ROC superset template missing from the stream.

Commercial databases such as Microsoft Access and Oracle, when populated with historical information, can be used as the ROC dB 210. However, a more efficient in-house database can also be created.

As set forth in FIG. 2, the second component of the ROC system 2000 is an application, referred to herein as the ROC property calculator 220, which takes stream molecular composition and returns stream bulk property values, such as weight fraction sulfur ("wtfrac sulfur"). Commercially available software, such as SimSci's ROMeo or PRO/II and AspenTech's AspenPlus can provide this functionality. As will be appreciated by those skilled in the art, the interface to the ROC property calculator 220 can vary greatly as it is dependent on the particular commercial or in-house package selected to make the calculations. In other words, one can calculate properties such as density or viscosity or cloud point with any of the aforementioned commercial software, or custom software, but the inputs required by the software will vary depending on the particular equation used by the computer program doing the calculation.

As set forth in FIG. 2, the third component of the ROC system 2000 is a first network service programming interface, referred to herein as the query interface 230, on a network 225 that allows users to query the ROC dB 210 and the ROC property calculator 220 for information about a given stream by providing a unique stream identifier and timestamp. Users of the query interface 230 can include individuals 205A and other programs 205B—including programs in the ROC engine 270 discussed below. The query interface 230 can be integrated with other interfaces (shown in FIG. 2) or exist as a standalone interface (not shown).

A first function that can be accomplished through the query interface 230 is simply the retrieval of detailed composition and other stream data stored in the ROC dB 210. The information retrieved can be used, for example, by plant historians and by applications, including RTOs, that model process unit operation.

A second function that can be accomplished through the query interface 230 is to request the calculation of bulk stream properties from the detailed composition and other stream data stored in the ROC dB 210, such as weight percent sulfur, via the ROC property calculator 220. For example, a user can request a bulk stream property such as octane for a given stream (e.g., a reformate stream) over a given period of time (e.g., a three month period). To perform this purpose, the query interface 230 first obtains the stream compositions over the given time period from the ROC dB 210 and then obtains the requested property for the stream compositions from the ROC property calculator 220.

A third function that can be accomplished through the query interface 230 is to convert a detailed stream composition in the ROC dB 210 into lumped component slates. For example, a user can convert a stream composition in the ROC dB 210 into lumped component slates to run an FCC process model. In general, to run an FCC process model, the detailed composition in the ROC dB 210, which contains thousands of components, must be mapped to the more reduced lumped component slate required by the FCC model. The query interface 230 provides this functionality. A separate interface call is written for each lumped component slate, where the logic for mapping the detailed composition to the lumped component slate is provided by the developer of the model which uses the reduced lumped component slate.

As set forth in FIG. 2, the fourth component of the ROC system 2000 is a second network service programming interface, referred to herein as the expansion interface 240, to allow a user on a network 225 to expand, or de-lump, a lumped component slate (i.e., lumped stream composition) to provide a ROC superset representation of the stream. Users of the expansion interface 240 can be individuals 205A or programs 205B—including the programs in the ROC engine 270 discussed below. The expansion interface 240 can be integrated with other interfaces (shown in FIG. 2) or exist as a standalone interface (not shown).

The expansion interface 240 is necessary, for instance, when a component slate originates from a modeling application, such as a real time optimization application, that draws feed stream data from the ROC dB 210 but runs fewer component characterizations than the ROC superset template. In other words, if the feed stream data is lumped, e.g., by the query interface 230, then any product stream data obtained will also be lumped and, in order to put the product stream data into the ROC dB 210, the product stream data needs to be delumped. For example, components have to be lumped for an FCC real time optimization model based on a 1,000 components that draws from a ROC dB 210 that characterizes 10,000 components. Therefore, to put molecular component data on a product stream obtained from the FCC model into the ROC dB 210, assuming the FCC model itself does not have suitable delumping capability, the product stream information from the FCC model has to be delumped.

A separate interface call must be written for each lumped component slate to expand the model product streams to a more detailed composition. The logic for expanding the lumped component slate for the product stream is dependent on the reaction chemistry applied to the feed. For example, both hydroprocessing and FCC models have been written— and are commercially available—that utilize lumped component slates, but the method used to expand the product slates obtained from these models differs because the reaction chemistry in the process units being modeled differs More particularly, for a hydroprocessing model, a detailed analysis of a "typical" product stream from the process unit, expressed in accordance with the ROC superset template, may be used to create the delumping rations used to expand the lumped product component slate to a ROC superset representation of the product stream. However, FCC models exist that require little lumping of lighter components and, since an FCC cracks heavier components into lighter components, any lumped heavier components in a product stream are principally unconverted feed. Therefore, in such cases, the delumping ratios used to expand the product composition can be calculated directly from a detailed ROC superset representation of the feed. Preferably, the strategy for delumping product streams uses static ratios—as this is the simplest way to perform the function—and basically reverses the logic in the algorithm used to lump the feed streams.

As set forth in FIG. 2, the fifth component of the ROC system 2000 is a third network service programming interface, referred to herein as a mapping interface 250, that allows users on a network 225 to map an arbitrary detailed composition to the ROC superset template. Users of the mapping interface 250 can be individuals 205A or programs 205B— including the programs in the ROC engine 270 discussed below. The mapping interface 250 can be integrated with other interfaces (shown in FIG. 2) or exist as a standalone interface (not shown).

The mapping interface 250 is most often necessary when an entirely new crude oil feed is introduced to the refinery. For example, if an arbitrary crude assay has 10,100 components, and the ROC superset template only maps 10,000 components, then an application program in the mapping interface 250 lumps the extra components in the assay to conform with the ROC superset template. In other words, any components in the 10,100 components that are not matched in the 10,000 component ROC superset template, have to be matched with the best fit within the 10,000 component ROC superset template. Obviously, the larger the ROC superset template, the less this activity becomes necessary. However, some companies, such as Exxon Mobil Corporation, obtain extremely detailed assays—meaning that the ROC superset template is rarely as detailed as the crude assay because the ROC superset template only needs to be as detailed as the requirements for the models that pull information from the ROC db 210. Preferably, the mapping interface 250 uses a process called "structure oriented lumping." (See, e.g., Quann, R J, Jaffe S B, Structure-oriented lumping: describing the chemistry of complex hydrocarbon mixtures, I&EC Res 31:2483-2497 (1992), the entirety of which is incorporated herein by reference.)

As set forth in FIG. 2, the sixth component of the ROC system 2000 is a fourth network service programming interface, referred to herein as the population interface 260, to allow users on a network 225 to populate the ROC dB 210 with detailed product stream composition data and other data with a unique product stream identifier and timestamp. Preferably, the population interface 260 is only called by the ROC engine 270 (discussed below). The population interface 260 can be integrated with other interfaces (not shown) or exist as a standalone interface (shown in FIG. 2).

For example, using the ROC method, a RTO or shadow model for a process unit, using the query interface 230 can pull information on the composition of a feed stream from the ROC dB 210 once an hour using a unique stream identifier and timestamp. The RTO or shadow model then runs a prediction of product streams from the refinery which, in accordance with the ROC method, is reconciled with other models and data on actual product stream properties. The population interface 260 is used to push this reconciled product stream data into the ROC dB 210 using a unique stream identifier and time stamp. The ROC dB 210 thereby contains dynamically updated information on the composition of product streams flowing from the process unit.

As set forth in FIG. 2, the seventh component of the ROC system 2000 is an application, referred to herein as the ROC engine 270, which automatically calculates the detailed stream compositions and bulk properties for major refinery streams and updates the ROC dB 210 using the population interface 260. The ROC engine 270 is described in more detail in the next section of this text.

4.4 The Rigorous On-Line Composition (ROC) Engine i. ROC Engine Generally

The ROC Engine 270, in general, comprises one or more molecular accounting tools. The ROC Engine 270 receives input stream composition and properties from refinery crude tracking systems (e.g., AspenTech's ORION), on-line analyzers, lab analyses and other monitoring tools and then reconciles stream properties with the compositional predictions of its own internal models. Ideally, the ROC Engine 270 models a blend of detailed molecular compositions provided by the current crude recipe, and tracks the molecules through the unit operations by mixing, splitting, and cutting streams and stream components in a manner that provides a best match to either measured refinery stream properties or stream properties from an on-line RTO. Since the ROC Engine 270 is built with commercially available software, communications between the on-line RTO, lab, and on-line measurements are available through various means, the most common being commercial databases such as Honeywell's PhD or Oracle dB. The reconciled product stream composition is then available for other purposes, such as use in molecular component models of processes that occur downstream of the process unit.

The ROC engine 270 is built on a commercially available platform, such as SimSci's ROMeo or AspenTech's AspenPlus. The ROC engine 270 contains, or is in communication with, a program that models a process unit—which may be an RTO for the process unit, other ROC engines, a process health monitoring tool, database of historical plant measurements and lab analyses, or a combination thereof. The ROC engine 270 also generally includes custom models (described below) that model relevant upstream processing, such as stream mergers, stream splits and component splits, and replace the basic source, mixer, and splitter models provided by the commercial platforms.

All sections of the ROC Engine 270 utilize a ROC superset representation of each slate as well as bulk property correlations performed by the ROC Property Calculator 220. The number of components desired in the ROC superset template precludes the use of a typical "stream model" construct employed in platforms such as SimSci's ROMeo or AspenTech's AspenPlus. In other words, the typical "stream model" platforms require thermodynamic calculations that cannot be solved for a large number of streams with 100's or 1000's of components. In contrast, the models in the ROC engine 270 are molecular accounting tools that don't require thermodynamic calculations. Taking advantage of this simplified construct, custom models are built to perform similar functions to the commercial platforms' basic source, mix and splitter models, without the corresponding thermodynamic equations.

The ROC engine application can be triggered to automatically run based on events such as the successful completion of an RTO system cycle. This functionality is part of commercially available RTO platforms, so the ROC Engine can be setup to run multiple times a day to automatically populate the ROC dB with the most recent estimate of stream composition and bulk qualities.

Obviously, the exact nature of the ROC engine 270 for each process unit or group of process units will vary depending on the exact nature of the process unit or units being modeled. Therefore, for the purposes of further illustration, a ROC engine 270 for a typical APS unit, which is a process unit common to every refinery, is described below.

ii. Illustrative APS ROC Engine

Figure 3:
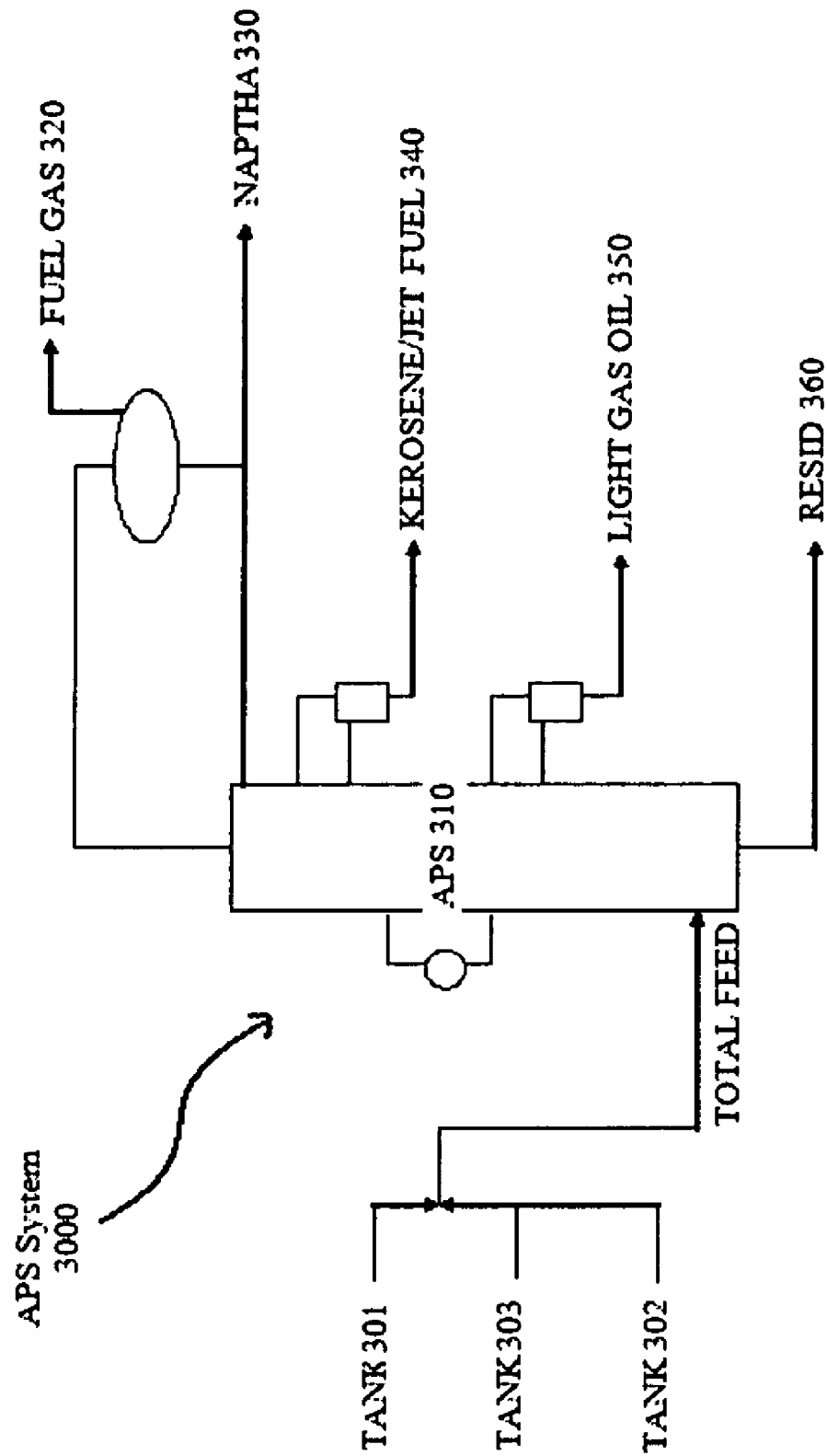
FIG. 3 illustrates stream flow in a typical APS system.

FIG. 3 describes a typical APS system 3000. In FIG. 3, three tanks, namely Tank 301, Tank 302 and Tank 303 provide individual or mixed feed streams to an APS tower 310. The APS tower 310 then cuts the feed streams into fuel gas 320, naphtha 330, kerosene/jet fuel 340, light gas oil 350 and resid 360.

Figure 4:
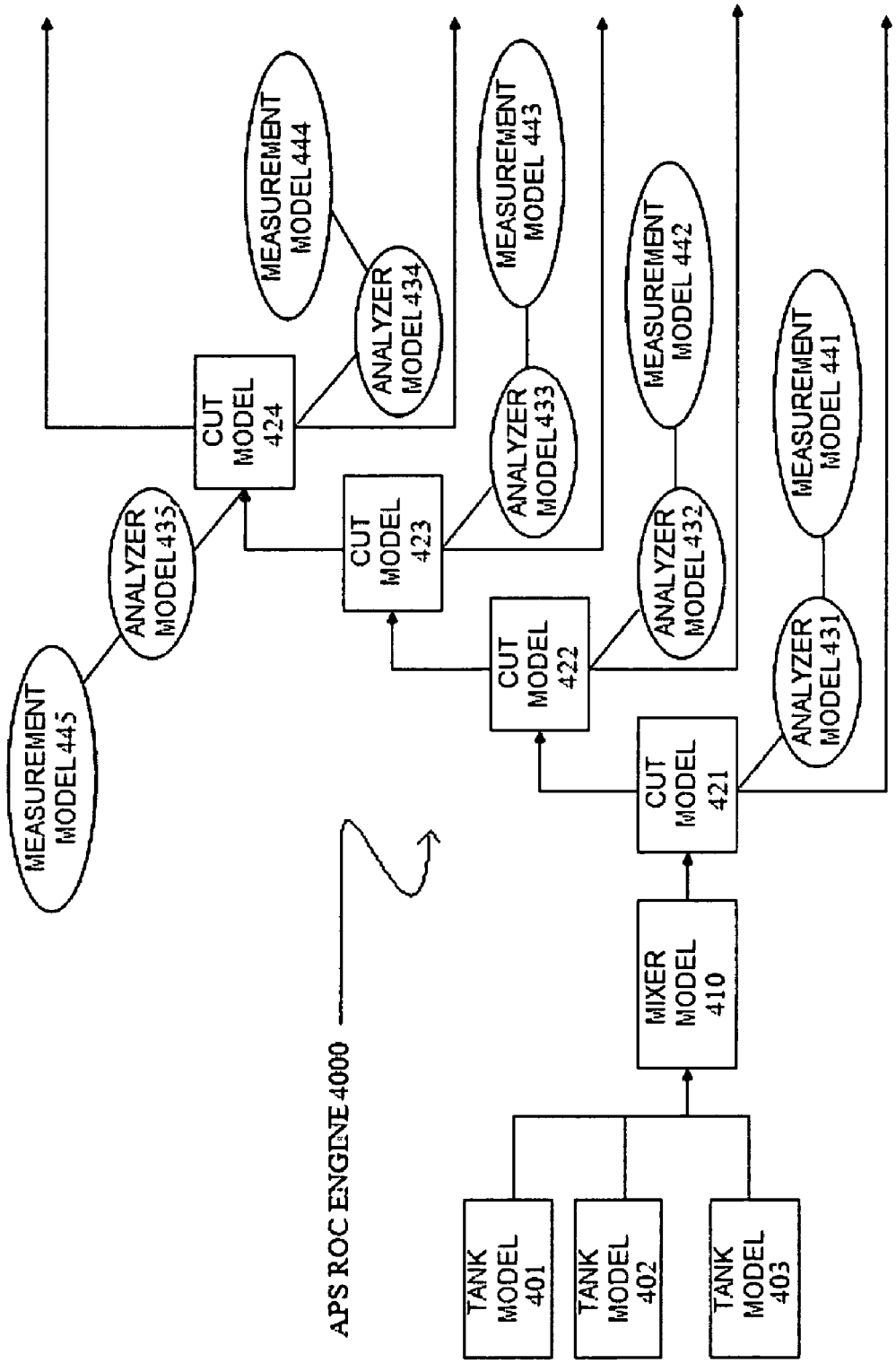
FIG. 4 illustrates the interrelation between components in a composition processing engine used in one embodiment of the invention for the APS system described in FIG. 3.

FIG. 4 illustrates the interrelation between components in an APS ROC engine 4000 used to track the detailed composition of streams to and through the APS tower 310 in FIG. 3. APS ROC Engine 4000 comprises a number of modules. These and other modules are discussed below.

a. Crude Assay Composition and Property Files

The first module in a typical APS ROC engine 4000 is a collection of binary files containing detailed crude assay compositions (not shown in FIG. 4) mapped to the ROC superset template as well as a collection of binary files containing crude assay bulk properties that cannot be calculated from the composition using the ROC property calculator 20 (e.g., weight fraction asphaltenes). These binary files are created using a unique identifier for each crude assay, which allows the assay data to be retrieved from the files efficiently. Each binary file containing a crude assay composition is referred to herein as a ROC assay file. Each binary file containing a crude assay bulk property is referred to herein as a ROC bulk property file. A conventional crude assay library can be formatted in this matter to avoid the need to create and populate a separate database.

b. ROC Component Property Repository

The second module in a typical APS ROC engine 4000 is a ROC component property repository (not shown in FIG. 4).

Many custom models within an APS ROC engine 4000 may require properties for each component in the ROC superset representation of the feed stream, such as normal boiling point (NBP), specific gravity (SPGR), and molecular weight (MW). These properties are stored for each component in the ROC superset template (e.g., if the ROC superset template characterizes 10,000 components, then these properties will be determined and stored for each of the 10,000 components). For ease of maintenance, it is desirable to have only one copy of the component properties in the application. Therefore, the ROC component property repository is a custom model without any equations. During model initialization, it loads the component properties into local parameters. These component properties can be either read in from a file, or stored in a library or DLL. The custom model should be written in such a way as to allow all other custom models to reference the parameter values. In SimSci's ROMeo platform, this is accomplished using a reference pointer.

c. Tank Model

The third module in a typical APS ROC engine 4000 is a tank model. For example, in FIG. 4, the APS ROC Engine 4000 contains tank models 401, 402 and 403. The APS ROC engine 4000 may have multiple tank models depending on the number of tanks in the process being modeled. The purpose of each tank model is to mimic the composition in each crude tank. For example, tank models 401, 402 and 403 in FIG. 4 represent the crude oil feed in each of tanks 301, 302 and 303, respectively, of the APS system 3000 in FIG. 3. The tank model input is the crude recipe (i.e., the weight fraction of each crude present in the tank and its corresponding assay identifier). During initialization, each tank model reads the crude assay composition from the ROC assay file and calculates the tank composition as a ROC superset representation by blending the composition of each crude oil in the tank by the weights provided in the crude recipe. The output of the model is the component weight fractions of the blend. In addition, this model contains the stream mass flow, which can be provided directly through on-line measurement or indirectly through an RTO for the APS unit that communicates with an on-line analyzer.

d. Source Model

The fourth module in a typical APS ROC engine 4000 is a called a source model (not shown in FIG. 4). The purpose of the source model is to mimic process streams other than virgin crude stored in the tanks. Process streams other than virgin crude are also potential feeds to the atmospheric crude distillation tower, such as recycle streams and imported feeds for which detailed assay data isn't provided. The detailed ROC superset representation of the composition of these streams may be obtained from a variety of sources, such as static references, outputs of process models, or FTIR Virtual Assay Technology. Configuration information in this model determines whether the composition is to be read from the ROC dB 210 or a text file. The compositions can be any arbitrary detailed composition. The mapping interface 250 described above is used to convert the inlet composition to conform with the ROC superset template. In addition, this model contains the stream mass flow, which can be provided by either a direct measurement or an on-line RTO of the atmospheric crude distillation column.

e. Mixer Model

The fifth module in a typical APS ROC engine 4000 is called a mixer model. The purpose of the mixer model is to mimic the blending of different streams. A ROC engine may have multiple mixer models depending on the number of mixing points in the process being modeled. For example, in FIG. 4, the APS ROC engine 4000 contains a single mixer model 410. The single mixer model 410 mimics the stream flowing from the point where the three feeds from tanks 301, 302 and 303 in the APS system 3000 of FIG. 4 combine to create a total feed for the atmospheric distillation column 310. The mixer model input is the mass flow and composition in weight fraction for one or more streams. This model blends the composition by weight, and its output is the mass flow and composition in weight fraction of the blended product stream. The mixer model employs the following formula:

$$\text{Weight Fraction component }(i) = \sum_{j=1}^{n} \text{weightfraction}(i,j) * \text{MassFlow}(j)$$

where i equals the component and j equals 1 to n feed streams.

f. Splitter Model

The sixth module in a typical APS ROC engine 4000 is called a splitter model. The purpose of the splitter model is to mimic a point where a given stream splits into multiple streams without undergoing a change in composition. In other words, the splitter model mimics a point where a single stream reaches a fork and splits into two or more streams (e.g., 20% goes in one direction and the remainder goes in another direction) and no change in composition otherwise occurs. An APS ROC engine 4000 may have multiple splitter models depending on the number of split points in the process being modeled. The APS ROC engine 4000 in FIG. 4 does not show a splitter model because no such split occurs in the APS system 3000 of FIG. 3. However, FIG. 3 represents a relatively simple APS design. It is not unusual for such splits to occur upstream from the APS in more complicated systems.

The input to each splitter model is the mass flow and composition in weight fraction of the inlet stream and either the split ratio or mass flow of "n−1" product streams. The model output is the mass flow of each product stream, as calculated from the inlet mass flow and split ratios or product mass flows. For example, mass flow can be calculated by the following formula:

Mass Flow Stream (i)=Inlet Mass Flow*Split Ratio Stream (i)

where i equals 1 to n and n represents the number of product streams off the splitter. Since no change in composition occurs, the product stream compositions in weight fraction is equal to the inlet composition in weight fraction.

g. Component Splitter Model

A seventh module in a typical APS ROC engine 4000 is called the component splitter model. The purpose of the component splitter model is to mimic a point (e.g., at a stripper) where selected components (e.g., water or $H_2S$) are split out of a stream so that the stream undergoes a change in composition. An APS ROC engine 4000 may have multiple component splitter models depending on the number of component split points in the process being modeled. The APS ROC Engine 4000 in FIG. 4 does not show a component splitter model because no such split occurs in the APS System 3000 of FIG. 3. However, FIG. 3 represents a relatively simple APS design. It is not unusual for component splits to occur upstream from the APS in more complicated systems.

The input to each component splitter model is the mass flow and composition in weight fraction of the inlet stream, and the split ratios for components to be removed from the inlet stream. Configuration of the component splitter model specifies which components are to be separated from the inlet stream. This model has two outlet streams, one containing the components to be separated from the main stream, and the second containing the remaining components. The component mass flows in the first stream are calculated in the following manner from the inlet mass flow, composition, and component split ratio:

Mass Flow Comp i=(Inlet Mass Flow)×(Inlet Wtfrac Comp i)×(Split Frac Comp i)

where i equals 1 to n and n represents the number of the product streams. The composition and mass flow of the second product stream is calculated via mass balance.

h. Cut Model

The eighth module in a typical APS ROC Engine 4000 is called a cut model. The purpose of the cut model is to mimic the behavior of the distillation column or flash drum. A ROC engine may have multiple cut models depending on the number of cuts in the process being modeled. For example, in FIG. 4, the APS ROC Engine 4000 uses cut models 421, 422, 423 and 424 to mimic the cuts made in the APS system 3000 of FIG. 3 by the distillation unit 310. Cut model 421 mimics the resid cut, whose residue is the resid stream 360 in FIG. 3. Cut model 422 mimics the light gas oil cut, whose residue is the light gas oil stream 350 in FIG. 3. Cut model 423 mimics the kerosene/jet oil cut, whose residue is the kerosene/jet oil stream 340 in FIG. 3. Cut model 424 mimics the naphtha cut, whose residue is the naphtha stream 330 in FIG. 3 and whose precipitate is the fuel gas stream 320 in FIG. 3.

Inputs to each cut model include the inlet mass flow and composition in weight fraction and the parameters of a short-cut distillation modeling method such as the Nm method. The output is the mass flow and composition in weight fraction of the overhead and bottoms product streams. Equations used to calculate the product stream compositions are dependent on the short-cut method chosen. Component normal boiling points are obtained by referencing the ROC component property repository. The Nm approach is based on a theoretical analysis of a tower operating at full reflux. A discussion of the basic equations utilized in the Nm approach can be found under "Fenske-Underwood-Erbar-Maddox Method" in Perry's Chemical Engineer's Handbook (7th ed.), edited by Perry, R. H. and Green, D. W., McGraw-Hill (1997), the entirety of which is hereby incorporated by reference. There are two parameters in the Nm method, the first is a cut point temperature, which is the boiling point of the component that will partition equally between the overhead and bottoms product stream. The second parameter, called the "Nm", refers to the minimum number of theoretical stages and determines the efficiency of the cut. The Nm method, as well as all other shortcut distillation methods, estimates the fraction of each component in the overhead product stream. The fraction of each component in the bottoms product stream is then calculated to satisfy the material balance.

i. Analyzer Model

The ninth module in a typical APS ROC engine 4000 is called an analyzer model. The purpose of the analyzer model is to mimic bulk properties. For example, the ROC engine, by and large, uses weight percent and mass flows. However, one may need to calculate a volumetric flow to reconcile data obtained from an RTO application. The analyzer model can be configured to calculate bulk properties such as volumetric flow at standard conditions and distillations. (See, e.g., ASTM D2887, D86, D1160, and D6352.) A ROC engine may have multiple analyzer models depending on the number and type of conversions that need to be made. For example, in the APS ROC engine 4000 in FIG. 4, for each cut generated by each cut model (421, 422, 423 and 424) there is also an analyzer model (431, 432, 433, 434 and 435) that derives mass flow and distillation values for the cuts. This information is then used in a reconcile case (discussed below) between the APS ROC engine 4000 and data obtained from a real time optimization application for the atmospheric distillation column 310 in the APS system 300 of FIG. 3.

Inputs to each analyzer model are the mass flow and stream composition in weight fraction. Component properties used in the bulk property calculations are obtained from the ROC component property repository. Each analyzer model must be configured to specify the stream as either liquid or vapor phase if volumetric flow at standard conditions is selected. Volumetric flows for mixed phase streams are not available in this model and are typically not measured in refineries. The following formulae for calculating the volumetric flows can be utilized:

Liquids: Vol Flow=Mass Flow/Stream SPGR
Vapor: Vol Flow=Mass Flow*Std Molar Volume/Stream MW where "Stream SPGR" equals $$1/(\sum_i [weightfraction(i)/SPGR(i)])$$

and "Stream MW" equals $$1/\sum_i [weightfractio(i)/MW(i)]$$

and i equals 1 to n, where n is the number of components in the ROC superset template.

The stream distillations can be modeled directly from the stream composition and component NBP (measured in accordance with ASTM D2887, D86, D1160, or D6352). For purposes of an analyzer model in the APS ROC Engine 4000, the distillation points are calculated at fixed weight, or volume, percents (0.5%, 5%, 10%, 30%, 50%, 70%, 90%, 95%, and 99.5%). Several commercially-available products can be used to calculate ASTM distillations from composition, such as SimSci's PRO/II. The analyzer model can either call one of these commercially-available packages directly, or contain its own algorithm for more efficient calculations. The algorithm should include a calculation of the stream true boiling point curve (TBP) by weight. A TBP by weight provides the temperatures at which the specified sample weight percent is in the vapor phase at 1 atmosphere pressure. The TBP by weight is calculated from the components' NBP and weight fraction by ordering the components by ascending NBP. The cumulative weight percent is calculated for each component, and the temperature corresponding to the desired "percent off" listed above is stored. If the desired weight percent in the vapor phase points fall between component cumulative weights, the corresponding TBP is obtained by linearly interpolating between the component NBPs. For streams with a significant amount of naphtha-range material (<400° F.), a more detailed algorithm using component boiling widths is required to accurately estimate the TBP temperatures. This algorithm is much more computationally intensive, since multiple components boil over the same temperature ranges. Generally, a normal distribution is assumed to determine how much of a component boils between the start of its component boiling range and a temperature within its boiling range. The TBP by weight is then converted to the chosen ASTM distillation method. Chapter 3 of the API Technical Databook, published by the American Petroleum Institute, 5th ed. (May 1992), the entirety of which is hereby incorporated by reference, provides the equations and diagrams necessary to convert a TBP by weight to any of the above ASTM methods.

j. ROC dB Sink

The tenth module in a typical APS ROC Engine 4000 is called the ROC dB sink model (not shown in FIG. 4). The purpose of the ROC dB sink model is to allow a user (authorized individual or program) to update the ROC dB after the ROC engine runs. The ROC dB sink model is utilized for any stream used to populate the ROC dB. After each successful ROC engine solution, the mass flow, composition, and bulk properties of interest are written to the ROC dB for some streams. The ROC dB sink model performs this function, using the population interface 60. This model must be configured with a unique ROC dB stream identifier and time stamp for each stream.

k. The ROC Engine Reconcile Case

The modules discussed above are the building blocks of the APS ROC engine 4000. When combined in the correct sequence, they can be used as a molecular accounting tool to track individual molecules throughout a given window of refinery operations including the APS unit 310. The feed composition at the beginning of the refinery operations window is provided by the tank models (401, 402 and 402) and source models, whose product streams are then split, mixed, and cut to mimic the separations performed as the stream goes to and through the APS unit 310. The models move the molecules within and between the streams based on fixed parameters. The splitter model splits the inlet stream into two or more product streams based on split ratios, as does the component splitter model. The cut models (421, 422, 423 and 424) separate the components based on the short-cut distillation method parameters. In the case of the Nm shortcut method, these parameters are the cut point and Nm factor, or theoretical number of trays. The value of these model parameters determine how the molecules move to and through the process unit.

All commercial RTO platforms provide a mechanism to compare model variables to plant measurements. This functionality is provided via measurement models, which associate a plant "measured" value to a model variable. A bias variable in each measurement model is calculated to represent the difference between the plant's measured value and the model value.

The ROC engine uses measurement models provided by the commercial platform to connect the inputs from on-line analyzers, lab analyses, RTO systems, and monitoring tools to the ROC engine variables. For example, the RTO system can provide mass flows and TBP distillations for all of the ROC model product streams. If no RTO system is available, lab analyses can provide TBP or other distillations for some, or all, of the product streams. On-line flow measurements are typically available for most refinery streams. The values of these inputs are the "plant" values in the measurement models in the ROC engine, which are connected to the appropriate ROC models. For example, in the APS ROC engine 4000 of FIG. 4, measurement models 441, 442, 443, 444 and 445 reconcile data from the real time optimization application for the distillation column 310 in FIG. 3 with data predicted by the cut models 421, 422, 423 and 424, respectively, as converted to comparable values by the analyzer models 431, 432, 433, 434 and 435, respectively.

A "reconcile case" is run on the ROC engine application. During the reconcile case, fixed model parameters are the decision variables, meaning they are adjusted to minimize the value of the application objective function. The ROC engine objective function is the sum of the squares of the measurement model bias variables. The ROC engine fixed parameters in the splitter, component splitter, and cut models are therefore adjusted in the reconcile case to minimize the difference between the model and measured product stream qualities (mass flows, distillations). The reconciliation answer obtained provides a detailed composition, in the form of a ROC superset representation, for the product stream. The ROC dB sink model then populates the ROC dB with this information at the end of each successful solution.

iii. Extending The ROC Engine Downstream Of Crude Distillation Columns

Conventional RTO systems downstream of the APS system typically rely on static feed reference characterizations tuned to match current feed bulk properties, yields, and product qualities. These static feed reference characterizations, because they are not based on updated feed characterization information, often lead to sub-optimal solutions and non-robust behavior.

The ROC dB 210 provides a means to dynamically update the feed reference for streams located downstream of any given process unit including any given APS unit. This permits enhanced optimization of the downstream refinery units, facilitating the modeling of stricter environmental laws and regulations governing fuel components such as sulfur. Tracking the molecules through the crude distillation columns to the feed systems of downstream refinery units allows for more accurate tuning of reactor kinetics to match product qualities, enhancing the predictive quality of the reactor system to changes in operating conditions.

More particularly, upstream ROC engines provide inputs to downstream RTOs and/or ROC engines 270 (i.e., those RTOs and/or ROC engines 270 modeling refinery stream compositions downstream of the APS column). The downstream RTO systems generally receive and provide inputs to and from their corresponding ROC engines 270. For example, the downstream RTO systems provide mass flow and product distillation inputs for refinery streams. However, whereas feed composition in the APS ROC engine 4000 was modeled mainly via tank models, downstream ROC engines model feed composition mainly via source models. Source models are used to characterize the tuned feed composition and any reactor effluent compositions. Usually, the RTO system utilizes a lumped component slate. An expansion interface 240 is used by the source models to expand the RTO system's lumped product stream component slates to the ROC superset template used in the ROC engine.

4.5 Closing

All publications, patents and patent applications mentioned in this specification are herein incorporated by reference to the same extent as if each individual publication, patent or patent application was specifically and individually indicated to be incorporated by reference. No admission is made that any reference cited herein is prior art.

The present invention is not limited in scope by the specific embodiments described herein. Indeed, various modifications of the present invention, in addition to those described herein, will be apparent to those of ordinary skill in the art from the foregoing description and accompanying drawings.

Further, although the present invention has been described in the context of particular implementations in particular environments for particular purposes, those of ordinary skill in the art will recognize the that the usefulness of the invention is not limited thereto and that the present invention can be beneficially implemented in any number of environments for any number of purposes.

What is claimed is:

1. A method of predicting the molecular composition of streams in a crude oil refinery comprising the following steps:
   (i) storing, in a database, composition data for potential feed streams;
   (ii) selecting, from the database, composition data for feed streams flowing to a designated group of one or more refinery operations during a designated time period;
   (iii) obtaining from at least one real time optimization applications, analyzers, laboratory analysis, or combination thereof, property measurements of actual intermediate and/or product streams produced in, or by, the group of refinery operations during the designated time period;
   (iv) communicating the feed stream composition data selected in step (ii) above and the intermediate and/or product stream property data obtained in step (iii) above to a process engine that comprises one or more molecular accounting models for modeling changes in composition made in or by the designated group of refinery operations;
   (v) running the one or more molecular accounting models in the processing engine, using the feed stream composition data communicated in step (iv) above as an input to at least one molecular accounting model, to obtain a prediction of the composition of a stream formed in or by the designated group of refinery operations during the designated time period and then reconciling the prediction with actual intermediate and/or product stream property data; and
   (vi) storing the reconciled prediction of intermediate and/or product stream composition in a database.

2. The method of claim 1, comprising the additional step of selecting, from the database of step (vi), composition data on a feed stream flowing to a group of one or more refinery operations located downstream from the group of refinery operations designated in step (ii).

3. The method of claim 1 where the designated group of refinery operations comprises an atmospheric pipestill.

4. The method of claim 1, where each step is performed automatically.

5. The method of claim 1, where each step is performed on demand.

6. The method of claim 1 where the molecular accounting models do not perform any thermodynamic or kinetic calculations.

7. The method of claim 1, where the entire method is performed at least once an hour and takes less than thirty minutes.

8. The method of claim 1 where stream composition data stored in steps (ii) and (vi) is stored in accordance with a template that characterizes a sufficient number of molecular components in sufficient detail to provide or derive any data needed by any real time optimization application, process model and bulk property correlation that obtains molecular component data from the database.

9. The method of claim 8 wherein the template characterizes over 1000 components.

10. The method of claim 1 where the database of step (ii) and the database in of step (vi) are the same database.

11. The method of claim 1 where the database in of step (ii) and the database in of step (vi) are different databases.

12. A method of predicting the molecular composition of streams in a crude oil refinery comprising the following steps:
   (i) storing composition data for potential feed streams in a database;
   (ii) selecting, from the database, composition data for feed streams flowing to a designated group of one or more refinery operations during a designated time period;
   (iii) obtaining from at least one real time optimization application, analyzer, laboratory analysis, or combination thereof, property measurements of actual intermediate and/or product streams produced in, or by, the designated group of refinery operations during the designated time period;
   (iv) communicating the feed stream composition data selected in step (ii) above and the intermediate and/or product stream property data obtained in step (iii) above to a process engine that comprises one or more molecular accounting models for modeling changes in composition made in or by the designated group of refinery operations;
   (v) running the one or more molecular accounting models in the processing engine, using the feed stream composition data communicated in step (iv) above as an input to at least one molecular accounting model, to obtain a prediction of a intermediate and/or product stream composition formed in or by the designated group of refinery operations during the designated time period and reconciling the prediction with actual intermediate and/or product stream property data by (a) calculating predicted properties for the intermediate and/or product streams based on the predicted stream composition obtained by the molecular accounting models, (b) comparing the predicted stream properties to the actual stream properties, and (c) adjusting fixed model parameters in the molecular accounting models to generate a predicted composition of intermediate and/or product streams that minimizes the difference between predicted stream properties calculated there from and actual stream properties to obtain a best fit; and
   (vi) storing the reconciled prediction of the intermediate and/or product stream compositions in a database.

13. An assembly comprising:
   (i) a database that stores files describing feed stream composition as well as feed stream bulk property and component property information;
   (ii) a processing engine that comprises (a) one or more molecular accounting models that model a designated group of one or more refinery operations to predict product stream composition; and (b) one or more applications that reconcile predicted product stream composition with actual product stream properties by (1) calculating predicted properties for the product stream based on the predicted stream composition obtained by the molecular accounting models; (2) comparing the predicted stream properties to the actual stream properties; and (3) adjusting fixed model parameters in the molecular accounting models to generate a predicted product composition that minimizes the difference between predicted stream properties calculated there from and actual stream properties to obtain a best fit; and
   (iii) a database that stores reconciled product stream composition predictions communicated thereto by the processing engine.

14. The assembly of claim 13 wherein the molecular accounting models in the processing engine don't perform thermodynamic and kinetic calculations.

15. The assembly of claim 13 where each feed stream composition and each reconciled product stream composition is stored using a unique stream identifier.

16. The assembly of claim 13 where each reconciled product stream compositions is stored using a unique identifier and time stamp.

17. The assembly of claim 13 wherein said molecular accounting models include at least one model selected from tank models, mixer models, splitter models, component splitter models and cut models.

18. The assembly of claim 13 where database (i) and database (ii) are the same database.

19. The assembly of claim 13 where database (i) and database (ii) are different databases.

* * * * *